United States Patent [19]

Tomasella

[11] Patent Number: 5,290,937
[45] Date of Patent: Mar. 1, 1994

[54] RADIOLABELING OF PROTEINS USING ALKOXYPHENOL DERIVATIVES

[75] Inventor: Frank P. Tomasella, Englishtown, N.J.

[73] Assignee: E. R. Squibb & Sons, Inc., Princeton, N.J.

[21] Appl. No.: 975,455

[22] Filed: Nov. 12, 1992

[51] Int. Cl.$^5$ .................. C07D 207/40; C07C 69/76; A61K 43/00; A61M 36/14
[52] U.S. Cl. ........................................ 548/547; 560/75
[58] Field of Search ............... 534/10; 424/1.1; 548/547; 560/75

[56] References Cited

U.S. PATENT DOCUMENTS

| | | | |
|---|---|---|---|
| 3,718,686 | 2/1973 | Chodnekar et al. | 260/473 R |
| 3,957,833 | 5/1976 | Chodnekar et al. | 260/348 R |
| 4,021,535 | 5/1977 | Polito | 424/1 |
| 4,885,153 | 12/1989 | Wilbur et al. | 424/1.1 |

(List continued on next page.)

FOREIGN PATENT DOCUMENTS

WO9100295 1/1991 European Pat. Off.

OTHER PUBLICATIONS

Leslie A. Khawli et al., "Synthesis of $^{125}$I Labeled N-Succinimidyl p-Iodobenzoate for Use in Radiolabeling Antibodies", Nucl. Med. Biol. vol. 16, No. 7, pp. 727-733, 1989.

Alvin Y. Liu et al., "Chimeric mouse-human IgG1 antibody that can mediate lysis of cancer cells", Proc. Natl. Acad. Sci. USA, vol. 84, pp. 3439-3443, May 1987.

Ingegerd Hellstrom et al., "Highly Tumor-reactive, Internalizing, Mouse Monoclonal Antibodies to Le$^y$-related Cell Surface Antigens", Cancer Research 50, 2183-2190, Apr. 1, 1990.

Ingegerd Hellstrom et al., "Antitumor effects of L6, and IgG2a antibody that reacts with most human carcinomas", Proc. Natl. Acad. Sci. USA, vol. 83, pp. 7059-7063, Sep. 1986.

Steven T. Rosen et al., "Radioimmunodetection and Radioimmunotherapy of Cutaneous T Cell Lymphomas Using an $^{131}$I-Labeled Monoclonal Antibody: An Illinois Cancer Council Study", Journal of Clinical Oncology, vol. 5, No. 4 (Apr.), 1987; pp. 562-573.

Alan R. Fritzberg et al., "Approaches to Radiolabeling of Antibodies for Diagnosis and Therapy of Cancer", Pharmaceutical Research, vol. 5, No. 6, 1988, pp. 325-334.

Dennis Engler et al., "The Deiodination of the Iodothyronines and of Their Derivatives in Man", Endocrine Review, vol. 5, No. 2, 1984, pp. 151-184.

Michael R. Zalutsky et al., "A Method for the Radiohalogenation of Proteins Resulting in Decreased Thyroid Uptake of Radioiodine", Appl. Radiat. Isot. vol. 38, No. 12, pp. 1051-1055, 1987.

Frederick T. Wood et al., "The Radioactive Labeling (List continued on next page.)

*Primary Examiner*—Robert L. Stoll
*Assistant Examiner*—Lara E. Chapman
*Attorney, Agent, or Firm*—Theodore R. Furman, Jr.; Suzanne E. Babajko

[57] ABSTRACT

Novel compounds, useful as radiolabeling reagents, including an alkoxy group on the phenyl ring and having the formula

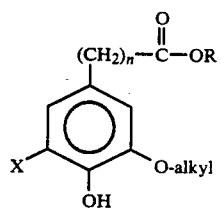

wherein X is a radionuclide are disclosed. The invention further includes novel radiohalogenated proteins as well as processes for preparing such reagents and radiohalogenated proteins.

5 Claims, No Drawings

U.S. PATENT DOCUMENTS 5,039,696  9/1991  Niwata et al. ............... 514/425
5,175,343  12/1992  Fritzberg et al. ............ 560/145
5,242,679  9/1993  Fritzberg et al. ............ 424/1.1
5,242,680  9/1993  Chorev ..................... 424/1.1

OTHER PUBLICATIONS of Proteins with an Iodinated Amidination Reagent", Analytical Biochemistry 69, pp. 339-349 (1975).

Andrew M. Keenan et al., "Monoclonal Antibodies in Nuclear Medicine", The Journal of Nuclear Medicine, vol. 26, No. 5, May 1985, pp. 531-537.

Jorge A. Carrasquillo et al., "Diagnosis of and Therapy for Solid Tumors with Radiolabeled Antibodies and Immune Fragments", Cancer Treatment Reports vol. 68, No. 1, Jan. 1984, pp. 317-328.

Michael R. Zalutsky et al., "Radiohalogenation of a Monoclonal Antibody Using an N-Succinimidyl 3-(Tri-n-butylstannyl)benzoate Intermediate", Cancer Research 48, Mar. 15, 1988, pp. 1446-1450.

Steven M. Larson, "Lymphoma, Melanoma, Colon Cancer: Diagnosis and Treatment with Radiolabeled Monoclonal Antibodies", Radiology, Nov. 1, 1987, vol. 65, No. 2, pp. 297-304.

Daniel F. Veber, "Peptide Synthesis from the Practitioner's Point of View", Peptides: Chemistry, Structure, Biology, Synthetic Studies, pp. 307-317.

A. E. Bolton et al., "The Labelling of Proteins to High Specific Radioactivities by Conjugation to a $^{125}$I-Containing Acylating Agent", Biochem. J. (1973) 133, pp. 529-539.

D. S. Wilbur et al., "Development of Stable Radioiodinating Reagent to Label Monoclonal Antibodies for Radiotherapy of Cancer", The Journal of Nuclear Medicine, vol. 30, No. 2, Feb. 1989, pp. 216-226.

S. J. DeNardo et al., "Radioimmunotherapy for breast cancer: treatment of a patient with I-131 L6 chimeric monoclonal antibody", The Int'l Journal of Biological Markers, vol. 6, No. 4, pp. 221-230.

A. Gruaz-Guyon et al., "Radiolabeled hapten-derivatized peptides for tumor imaging with bispecific antibody conjugates", Peptides 1990 pp. 822-825.

J. F. Eary et al., "Radiochemistry of Halogenated Antibodies", Antibodies in Radiodiagnosis and Therapy, Editor M. R. Zalutsky, pp. 83-102.

J. C. Sheehan et al. "Activated Cyclic Derivatives of Amino Acids", *J Am Chem Soc* 1959, 81, p. 6086.

Solomons, *Organic Chemistry 4th Ed.*, Table 12.2, p. 533.

RADIOLABELING OF PROTEINS USING ALKOXYPHENOL DERIVATIVES

FIELD OF THE INVENTION

The present invention relates to the radiolabeling of proteins, and more particularly concerns indirect radiohalogenation processes for proteins including reagents and products pertaining to same.

BACKGROUND OF THE INVENTION

Radiolabeled proteins have been investigated extensively over the past decade for a number of clinical applications. For example, radiolabeled monoclonal antibodies are being developed for therapeutic and diagnostic uses. Monoclonal antibodies having high specificity and affinity for antigens on tumor cell surfaces are considered desirable candidates as carrier molecules to which specific radionuclides can be attached for delivery of radioactivity to a cancer site for therapy or diagnosis.

Radiohalogens are known to possess utility in both therapy and diagnosis. For example $^{123}I$ has been proven useful for imaging, while $^{131}I$ can be used for imaging and more preferably for radiotherapy. Bromine radionuclides $^{75}Br$ and $^{76}Br$ are also useful in diagnosis, while $^{77}Br$ is used in radiotherapy. Fluorine-18 ($^{18}F$) and astatine-211 (211At) are also utilized in diagnostics and radiotherapy.

Processes for directly labeling proteins, such as antibodies, have proven to be difficult. Typically, the strong oxidation conditions involved in direct radiolabeling of an antibody have substantial adverse effects on the biological activity of the antibody. It is also known that radiohalogenation of antibodies occurs primiarily at the tyrosyl residues providing a less than stable bond. In vivo dehalogenation, rendering the imaging or therapeutic agent useless and causing possible toxicity to the patient may result.

Improvements have been realized with the development of indirect labeling techniques. These involve the prelabeling of a small molecule suitable for subsequent conjugation to a protein. An early series of small molecules useful for indirect labeling includes a phenol group for facile introduction of the radiohalogen. The exemplary member of this group is the commercially available Bolton-Hunter reagent

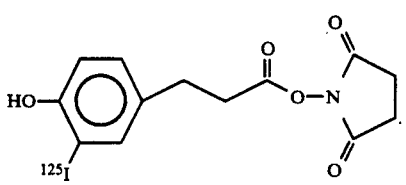

While these reagents greatly reduce the protein-damaging chemistry used in the direct labeling techniques, in vivo deiodination is still a problem. More recent reagents for indirect labeling include succinimidyl para-iodobenzoate

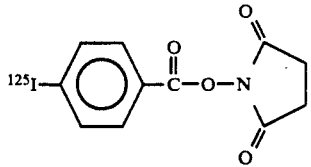

and succinimidyl para-iodophenylpropionate

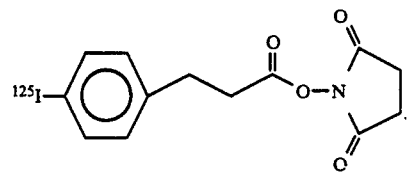

U.S. Pat. No. 4,885,153 discloses indirect radiohalogenating reagents of the formula

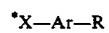

where *X is a radiohalogen, Ar is an aromatic or heteroaromatic ring which may include polar substituents, e.g., nitro, sulfonic acid, carboxylic acid or dialkylamino, and R is a short chain substituent which includes a functional group for conjugation to a protein.

SUMMARY OF THE INVENTION

In accordance with the present invention it has now been found that compounds including an alkoxy group at the 3 position of the phenyl nucleus, are useful for indirect radiohalogenation of proteins, e.g., monoclonal antibodies. The present compounds have the general structure

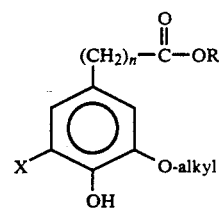

where
X is a radionuclide;
R is

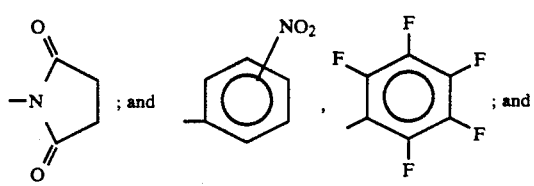

n=0 or 1 to 5

Processes for preparing the above compounds, processes using such compounds and the radiohalogenated proteins resulting therefrom are also a part of this invention.

DETAILED DESCRIPTION OF THE INVENTION

The present compounds useful as radiolabeling reagents, provide excellent in vivo stability against dehalogenation. Also, the process which uses these radiolabels to prepare radiolabeled proteins is a mild technique which is therefore protective of the biological activity of the protein. While the exact mechanism is not known, the enhanced protection against dehalogenation provided herein is believed to be attributable to proteins radiolabeled using compounds of formula I.

The novel radiohalogenated proteins of the present invention have the general formula

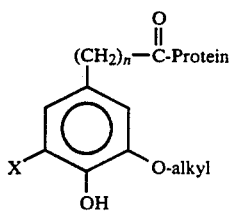
II wherein the protein may be linked to the molecule via a carrier.

The term radiohalogen as used herein for compounds of formula I, formula II and throughout this application refers to any radionuclide of any of the halogens. Exemplary radiohalogens include radionuclides of iodine, bromine, fluorine and astatine; and, more specifically, may include $^{123}I$, $^{125}I$, $^{131}I$, $^{75}Br$, $^{77}Br$, $^{18}F$ and $^{211}At$.

The term protein as used herein refers to any protein requiring conjugation with a radionuclide including but not limited to monoclonal antibodies and plasma proteins, polypeptides, hormones, carbohydrates and the like. Exemplary monoclonal antibodies include ChiL6, ChiBR96, murine L6, murine BR96.

The term carrier as used herein refers to any group coupled to a protein which can also be coupled to another molecule to provide a linkage between the protein and molecule. Suitable carriers include amino acid polymers, e.g., polylysine, carbohydrates, and the like.

The term alkyl as used herein, by itself or as part of another group, refers to branched and straight chain groups of up to 12 carbon atoms, and preferably of 1 to 8 carbons.

To prepare the compounds of formula I a compound of the formula

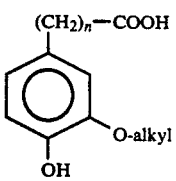
III is reacted with a compound of the formula

H—R  IV in a solvent, such as tetrahydrofuran, and preferably in the presence of a coupling agent, e.g., dicyclohexylcarbodiimide, to provide compounds of the formula

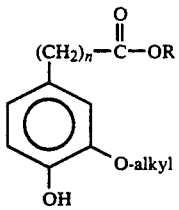
V

The intermediate of formula V is thereafter provided with a radionuclide, X, by known methods.

The desired formula I compound is typically radiolabeled prior to conjugation with the desired protein using procedures such as those described by Appl. Radiat. Isot., 1987, 38, 921-925, Int. J. Appl. Radiat. Isot., 1984, 35, 1129-1132, Czech. Patent CS 188692 B, 15 Jul. 1981, etc. For example, a desired compound of formula I can be treated with a source of radionuclide such as $Na^{125}I$ in one or more solvents and in the presence of a catalyst, e.g., HCl, $H_3PO_4$, $HAuCl_4$, $H_2PtCl_6$. Such procedures, as described in U.S. Pat. No. 4,885,153 and the examples herein, may typically incude the use of a phosphate buffer solution and are carried out in protic solvents such as water, methanol, ethanol or mixtures thereof, or non-protic solvents, e.g., $CCl_4$. A preferred method involves treating the compounds of formula V with known chloromine T solution in a solvent, e.g. dimethylformamide and with the use of a phosphate buffer. Acetic acid/solvent mixtures are also known to be employed when treating with the source of radionuclide to prevent unwanted hydrolysis of compound I.

Conjugation of the radiolabels of formula I of this invention with the desired protein is conveniently carried out by reacting an appropriate source of protein in the presence of a solvent with the radiolabeled compound of formula I, typically in the presence of an aqueous buffer solution to maintain a mild pH, preferably pH ~9.

Preferred radiolabeling reagents of the present invention are those of formula I wherein
n=0;
R is

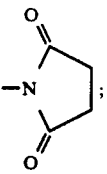

X is a radionuclide of iodine; and alkyl is methyl or ethyl.

The preferred radiolabeled proteins in accordance with the present invention are those "preferred" reagents above, conjugated with the chimeric monoclonal antibody L6 and the chimeric monoclonal antibody BR96.

The invention will now be further described with reference to the examples which follow.

EXAMPLE 1

$^{125}I$-Labeled N-succinimidyl-4-hydroxy-3-methoxybenzoate

A. N-succinimdyl-4-hydroxy-3-methoxybenzoate

To a solution of 4-hydroxy-3-methoxybenzoic acid (0.84 g, 5 mmol) and N-hydroxysuccinimide, (0.58 g, 5 mmol) in THF (3.5 mL) at 0° C. was added N,N'-dicyclohexylcarbodiimide (DCC), (1.20 g, 6 mmol). The reaction was stirred for 3 hours and allowed to warm to room temperature. The excess DCC was destroyed with the addition of acetic acid (0.1 mL). The mixture was diluted with ethyl acetate (6 mL) and filtered. The precipitate was washed with ethyl acetate (3 mL). The combined filtrate was concentrated to afford a crude material which was recrystallized from ethyl acetate (10 mL) and ether (5 mL) to afford 0.17 g of the title A product. A purified sample was obtained by recrystallizing a 50 mg portion which afforded 35 mg of the title A product.

B. 125I-Labeled N-succinimdyl-4-hydroxy-3-methoxybenzoate

To a solution of the title A product (25 μg, 0.094 μmol) dissolved in 5 μL of dry N,N'-Dimethylformamide (DMF) was added 2 μL (2 mCI) of Na$^{125}$I followed by 20 μL (0.18 μmol) of a chloramine-T solution dissolved in 50 mM phosphate buffer pH 7.5. After 30 seconds the reaction was quenched by the addition of 10 μL (0.21 μmol) of a Na$_2$S$_2$O$_5$ solution in 20 mM phosphate buffer pH 7.5. Immediately, the aqueous solution was extracted with 100 μL ethyl acetate. The ethyl acetate extract is dried with magnesium sulfate and filtered. The activity of the ethyl acetate extracted was 800 μCi.

EXAMPLE 2

Chi L6 conjugated with the Example 1 label

A portion (40 μL, 5 μg, 300 μCi) of the above Example 1 ethyl acetate solution was transferred to a 1 mL reactive vial. The ethyl acetate was evaporated by passing a stream of N$_2$ gas through the reaction vial connected to a granulated charcoal tube which serves as a trap for any volatile iodine. The ChiL6 (200 μg, 60 μL) in 50 mM borate buffer pH 8.8 was added to the above reactive vail and allowed to stir. The conjugation reaction was completed in three hours as determined by size exclusion chromatography with coupling efficiency of 24%. The radioiodinated protein was isolated from the lower molecular weight unbound radiolabel with a Sephadex G-25 column. The specific activity of the purified antibody was 0.31 μCi/μg.

EXAMPLE 3

Chi BR96 conjugated with the Example 1 label

The ethyl acetate solution containing the Example 1 product (150 μL, 20 μg, 170 μCi) was transferred to a 1 mL reactive vial. The ethyl acetate was evaporated by passing a stream of N2 gas through the reaction vial connected to a granulated charcoal tube. ChiBR96 (198 μg, 30 μL) in 50 mM borate buffer pH 8.8 was added to the above reactive vial and allowed to stir. The conjugation reaction was completed in three hours as determined by size exclusion chromatography with coupling efficiency of 9.3%. The radioiodinated protein was isolated from the lower molecular weight unbound radiolabel with a Sephadex G-25 column. The specific activity of the purified antibody was 2.0 μCi/μg.

What is claimed is:

1. A compound of the formula

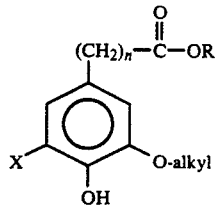

wherein
X is a radionuclide,
R is

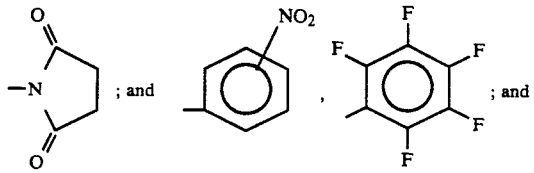

n=0 or 1 to 8.

2. The compound of claim 1 wherein X is selected from $^{125}$I, $^{131}$I, $^{123}$I, $^{75}$Br, $^{76}$Br and $^{77}$Br.

3. The compound of claim 1 wherein
X is a radionuclide of iodine;
n=0;
R is

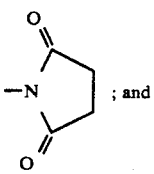

alkyl is methyl or ethyl.

4. The compound of claim 1 wherein X is $^{125}$I.

5. The compound of claim 1 having the name $^{125}$I-Labeled N-succinimidyl-4-hydroxy-3-methoxybenzoate.

* * * * *